(12) United States Patent
Kazanovicz et al.

(10) Patent No.: US 9,345,579 B2
(45) Date of Patent: *May 24, 2016

(54) TIBIAL TUBEROSITY ADVANCEMENT IMPLANT

(71) Applicant: MWI Veterinary Supply Co., Boise, ID (US)

(72) Inventors: Andrew J. Kazanovicz, Slatersville, RI (US); David J. Anderson, III, Suffield, CT (US)

(73) Assignee: MWI Veterinary Supply Co., Boise, ID (US)

( * ) Notice: Subject to any disclaimer, the term of this patent is extended or adjusted under 35 U.S.C. 154(b) by 15 days.

This patent is subject to a terminal disclaimer.

(21) Appl. No.: 14/532,572

(22) Filed: Nov. 4, 2014

(65) Prior Publication Data

US 2015/0057760 A1    Feb. 26, 2015

Related U.S. Application Data

(62) Division of application No. 14/293,128, filed on Jun. 2, 2014, which is a division of application No. 13/559,103, filed on Jul. 26, 2012, now Pat. No. 8,790,410.

(51) Int. Cl.
| | |
|---|---|
| *A61F 2/38* | (2006.01) |
| *A61B 17/80* | (2006.01) |
| *A61D 1/00* | (2006.01) |
| *A61F 2/30* | (2006.01) |

(52) U.S. Cl.
CPC ............. *A61F 2/389* (2013.01); *A61B 17/8095* (2013.01); *A61D 1/00* (2013.01); *A61F 2002/30062* (2013.01); *A61F 2002/30405* (2013.01); *A61F 2220/0008* (2013.01)

(58) Field of Classification Search
CPC .......... A61F 2/38; A61F 2/389; A61F 2/3868
See application file for complete search history.

(56) References Cited

U.S. PATENT DOCUMENTS

| | | | |
|---|---|---|---|
| 7,572,291 | B2 | 8/2009 | Gil et al. |
| 7,947,073 | B2 | 5/2011 | Gellman et al. |
| 8,790,410 | B2 | 7/2014 | Kazanovicz et al. |
| 2011/0319994 | A1 | 12/2011 | Tepic et al. |
| 2012/0197410 | A1 | 8/2012 | Horan et al. |
| 2013/0190886 | A1 | 7/2013 | Tepic et al. |
| 2014/0277545 | A1 | 9/2014 | Kazanovicz et al. |

OTHER PUBLICATIONS

Securos Orthopedic Resource Guide, "PLX MPL/LPL Spacer Implant", www.SECUROS.com, Jan. 2011, p. 56 (1 pg.).

*Primary Examiner* — Jason-Dennis Stewart
(74) *Attorney, Agent, or Firm* — Iandioro Teska & Coleman, LLP

(57) ABSTRACT

A tibial tuberosity advancement implant and method includes a spacer body made of biocompatible, biodegradable material and having a main section with at least one bony growth orifice therethrough and at least one fin extending from the main section by at least one connector. A metal clip is engageable with of the spacer body main section and includes spaced screw holes for securing the spacer body to the advanced tibial tuberosity and the tibia when the implant is placed in the space between the advanced tibial tuberosity and the tibia.

12 Claims, 4 Drawing Sheets

TIBIAL TUBEROSITY ADVANCEMENT IMPLANT

RELATED APPLICATIONS

This application is a divisional of U.S. patent application Ser. No. 14/293,128 filed Jun. 2, 2014, which hereby claims the benefit of and priority thereto under 35 U.S.C. §§119, 120, 363, 365, and 37 C.F.R. §§1.55 and 1.78, which is a divisional of U.S. patent application Ser. No. 13/559,103 filed Jul. 26, 2012 now U.S. Pat. No. 8,790,410, the benefit of and priority thereto claimed under 35 U.S.C. §§119, 120, 363, 365, and 37 C.F.R. §1.55 and §1.78, and both are incorporated herein by this reference.

FIELD OF THE INVENTION

The invention relates to tibial tuberosity advancement procedures in canines.

BACKGROUND OF THE INVENTION

During the tibial tuberosity advancement procedures in canines, the tibia is cut just behind the tibial tuberosity and the tibial tuberosity is advanced to achieve a perpendicular relationship between the tibial plateau slope and the patella tendon. A titanium or stainless steel implant (also called a cage or spacer) is placed between the advanced tibial tuberosity and the tibia and a plate is used to secure the tibial tuberosity to the tibia.

Over time, bony growth forms in and around the spacer. In the case of an infection or other problem, it can be very difficult to remove the spacer. As many as one in ten tibial tuberosity advancement procedures result in infection or rejection of the spacer implant.

Biocompatible and biodegradable materials are known for use in implants but an implant made of a plastic biodegradable material and designed like prior art metal implants may not be strong enough to maintain the tibial tuberosity in the advanced state as the canine recovers and becomes active. Injection molding limitations also prevent manufacturing a plastic implant designed like the prior art metal tibial tuberosity implant.

SUMMARY OF THE INVENTION

In one or more aspects of a preferred embodiment of the invention, a trimable tibial tuberosity advancement implant is molded using a biocompatible, biodegradable material so that in case of infection or the like only the metal clip portion of the implant need be removed (using, for example, minimal invasive surgery techniques). And yet, the implant spacer body is structurally sound until decomposition and bony ingrowth occurs between the advanced tibial tuberosity and the tibia.

Featured is a tibial tuberosity advancement implant comprising a spacer body made of biocompatible, biodegradable material. A main section has at least one bony growth orifice therethrough. At least one fin extends from the main section by at least one connector. A clip is engageable with the main section and includes spaced screw holes for securing the spacer body to the advanced tibial tuberosity and the tibia when the spacer body is implanted.

The clip is usually made of stainless steel or titanium. It preferably includes spaced ears each having a screw hole and upper and lower spaced spring arms interconnecting the spaced ears. Each spring arm then includes an outwardly curved portion including a central cut out and the spacer body main section slot includes spaced upper and lower tabs each received in a cut out of the clip.

The typical biocompatible, biodegradable material used includes polyglycolic acid and/or polylactic acid. Preferably, the spacer body main section includes at lease two spaced bony growth orifices, the spacer body main section has an isosceles trapezoid cross sectional shape, the fins are angled inwardly rendering the top of the implant longer and wider than the bottom and there is a top and a bottom cuttable connector for each fin to customize the length of the implant.

One example of a tibial tuberosity advancement implant in accordance with the invention includes a spacer body made of biocompatible, biodegradable material and including a main section having an isosceles trapezoid cross sectional shape with at least one bony growth orifice therethrough and a proximal slot. Inwardly angled fins extend from the main section rendering the top of the implant longer than the bottom. A clip is slideable into the proximal slot of the main section and includes spaced screw holes for securing the spacer body to the advanced tibial tuberosity and the tibia.

Another tibial tuberosity advancement implant made of biodegradable material includes a proximal face, a slot behind the proximal face for a metal clip, distal spaced cuttable fins, and bony growth orifices in a main body section between the proximal face and the distal fins. Typically, the implant is longer and wider at the top than at the bottom and the body section is configured as an approximation of a concrete block.

This invention also features a method comprising advancing the tibial tuberosity of a canine, implanting a biodegradable spacer to retain the tibial tuberosity in an advanced position, fixing the implant using a metal non-biodegradable clip connected to the spacer, promoting bony in-growth and degradation of the biodegradable spacer, and removing the metal non-biodegradable clip in the case of an infection or other problem.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features, and advantages will occur to those skilled in the art from the following description of a preferred embodiment and the accompanying drawings, in which.

DETAILED DESCRIPTION OF THE INVENTION

Figure 1:
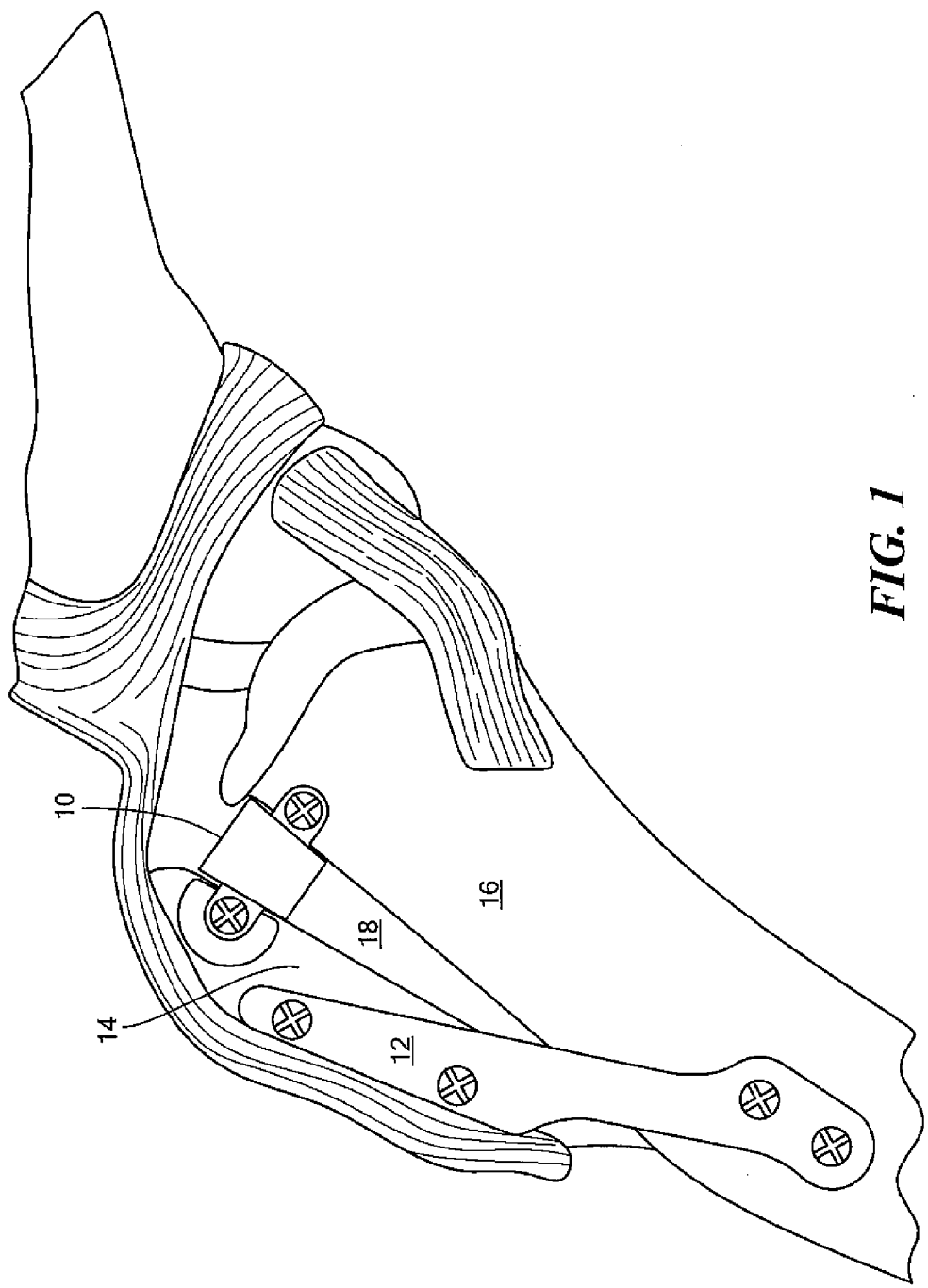
FIG. 1 is a schematic three dimensional side view of an implant between an advanced tibial tuberosity and the tibia of a canine.

FIG. 1 shows implant 10 used in a tibial tuberosity advancement procedure in accordance with the invention along with plate 12. Implant 10 is preferably injection molded using a biocompatible, biodegradable plastic material such as polyglycolic acid and/or polylactic acid. It may also include bone growth proteins and the like. Initially, implant 10 is structurally sound and correctly spaces the advanced tibial tuberosity 14 from the tibia 16 while the canine is recuperating and thereafter active. The implant has features which promote bony growth between the advanced tibial tuberosity and the tibia which over time fills space 18. Thereafter, the implant degrades and dissolves.

Thus, in the case of infection, rejection, or some other problems requiring removal of the implant, all that need be removed are the two screws and the metal clip portion of the implant. Minimally invasive surgical techniques can be used. In the prior art, as explained in the Background section above, the titanium or stainless steel implant was secured in the space 18 by bony growth and was very difficult to remove. Minimally invasive surgical techniques could not be used.

Figure 2:
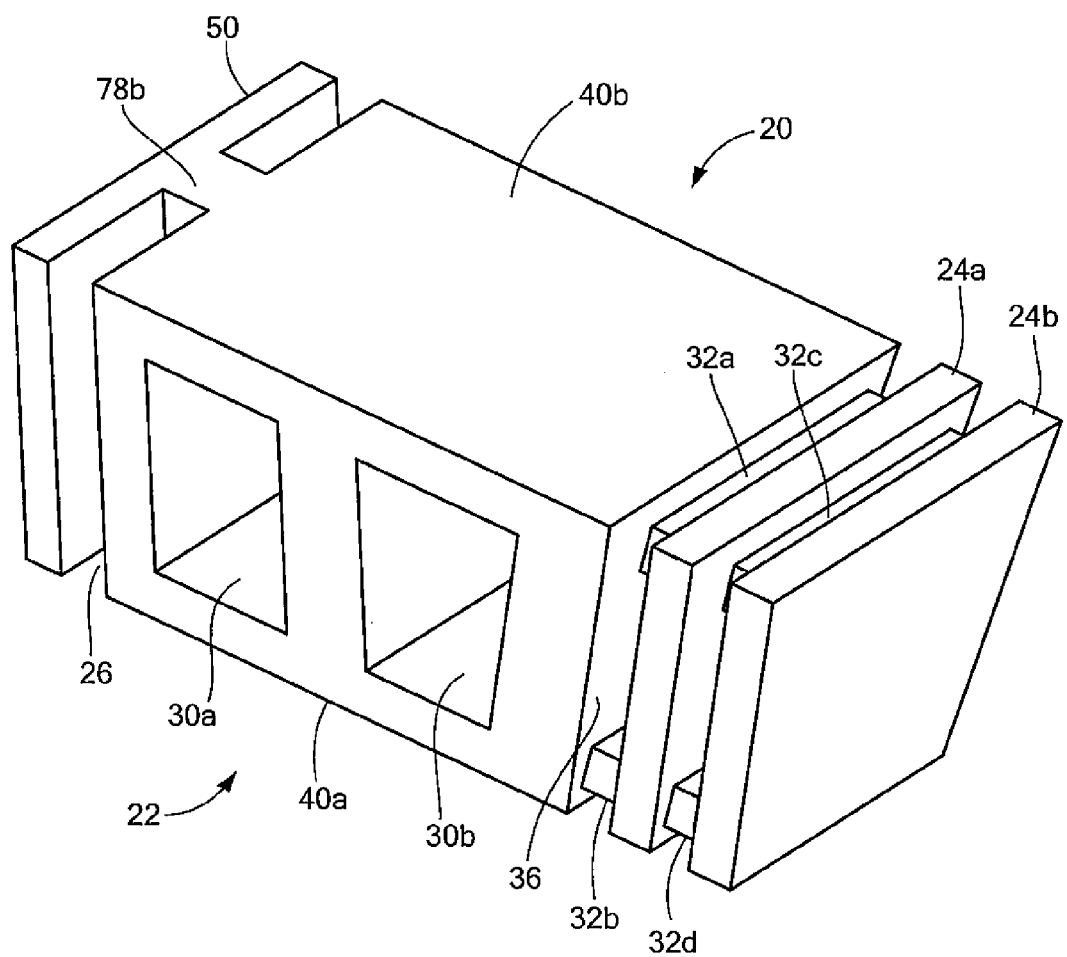
FIG. 2 is a schematic three dimensional side view of an example of a preferred version of a biodegradable implant in accordance with the invention.
Figure 3:
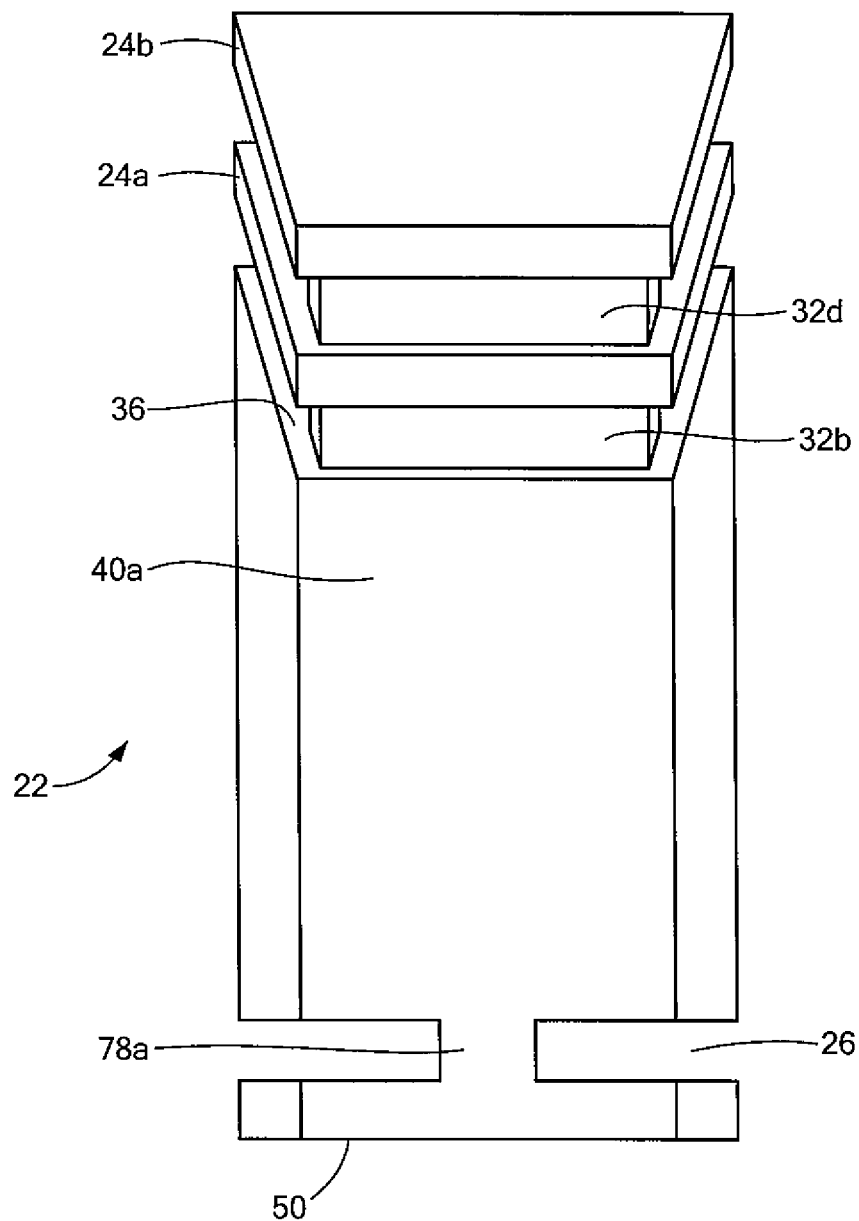
FIG. 3 is a schematic bottom view of the implant shown in FIG. 2.

One preferred version of the implant is shown in FIGS. 2-5. Structurally strong spacer body 20, FIGS. 2-3, is made of biocompatible, biodegradable material and includes main section 22 and distal fins 24a and 24b. Main section 22 has proximal slot 26 for clip 28, FIG. 4. Main section 22 also has bony growth orifices 30a and 30b therethrough designed to promote bone growth therein and around the implant. Section 22 somewhat mimics the configuration of a concrete block. Spaced fins 24a and 24b are also designed to promote bony growth in the space between main section 22 and fin 24a and in the space between fin 24a and fin 24b. Also, top and bottom connectors 32a and 32b (connecting fin 24a to main section 22) and top and bottom connectors 32c and 32d (connecting fin 24b to fin 24a) can be cut, as desired, to shorten the length of the implant for different size canines.

With both fins intact, the implant is 27 mm long; with fin 24b cut off, the implant is 24 mm long; and with both fins 24a and 24b cut off the implant is 21 mm long. In this way, one mold is effectively able to produce three different length implants. Other sizes are possible. Different width cages are possible.

Figure 5:
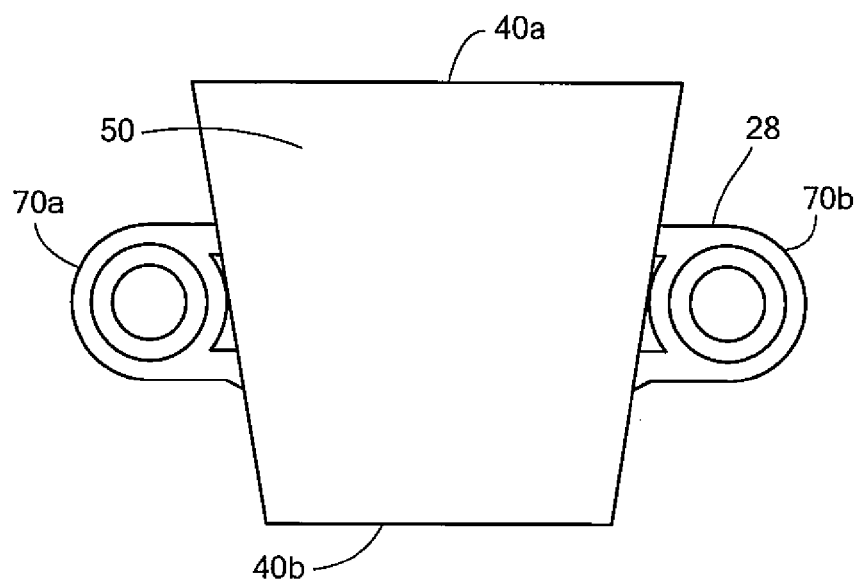
FIG. 5 is a schematic front view of the implant of FIGS. 2-3 with the clip of FIG. 4 inserted therein.

Fins 24a and 24b as well as distal wall 36 of main section 22 are angled inwardly at 25° with respect to vertical resulting in an implant with a shorter bottom surface 40a and a longer top surface 40b, FIGS. 3 and 5. Spacer body main section 22 also has an isosceles trapezoid cross sectional shape as does proximal face 50 (see FIG. 5) and fins 24a and 24b. As a result, the top of the implant is wider and longer than the bottom. The implant thus conforms to the shape of the space between the tibia and the advanced tibial tuberosity.

In one example, the implant was 27 mm long at the top, 22 mm long at the bottom, 9 mm wide at the top, and 7 mm wide at the bottom. Fin connectors 32 were 2.1 by 6 by 1.2 mm. Slot 26 behind proximal face 50 was 1.2 mm wide.

Figure 4:
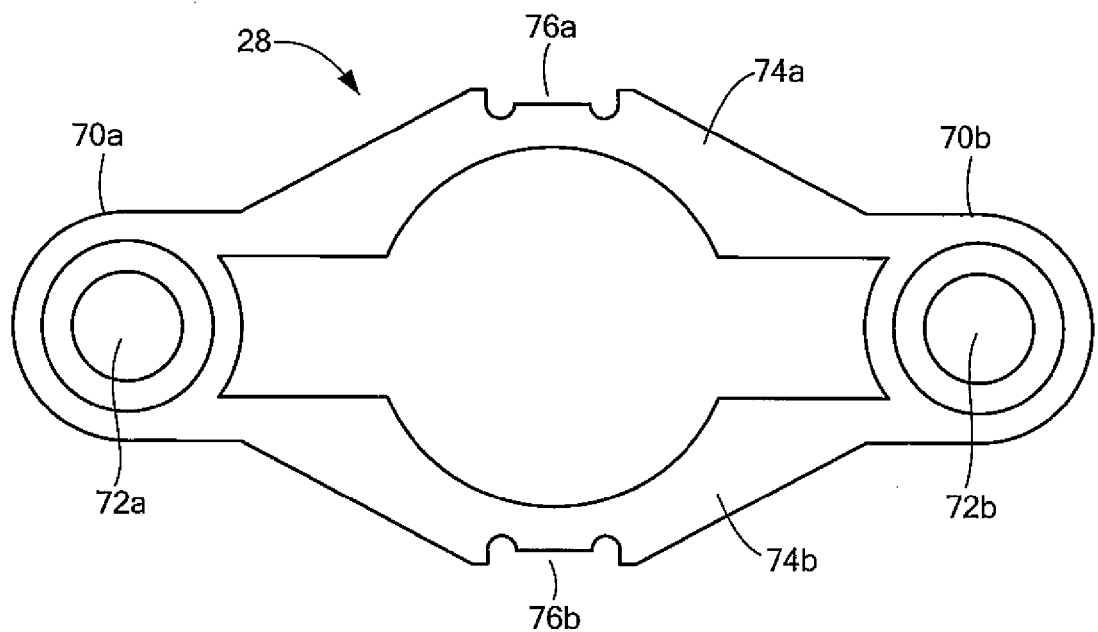
FIG. 4 is a schematic front view of an example of the clip portion of an implant in accordance with the invention.

Preferably, stainless steel or titanium 1 mm thick clip 28, FIG. 4 has spaced ears 70a and 70b each with a screw hole 72b and 72b, respectively. Curved upper 74a and lower 74b spring arms interconnect the ears 70. Each spring arm 74 includes central cut out 76a, 76b that receive therein centered tabs connecting proximal face 50, FIGS. 2-3 to main section 22. Bottom tab 78a is shown in FIG. 3 and top tab 78b is shown in FIG. 2. The clip spring arm cutouts are wider than the thickness of the tabs so clip 28 can be rotated slightly with respect to the spacer body. When clip 28 is inserted into spacer body slot 26, spring arms 74a and 74b are compressed towards each other. After insertion, the upper and lower tabs retained in the cutouts retain the clip in the spacer body.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A tibial tuberosity advancement implant comprising:
    a spacer body made of biocompatible biodegradable material and including:
        a main section with at least one bony growth orifice therethrough, and
        at least one fin extending from the main section by at least one connector; and
    a clip engageable with the main section and including spaced screw holes for securing the spacer body to the advanced tibial tuberosity and the tibia.

2. The implant of claim 1 in which the clip is made of stainless steel or titanium.

3. The implant of claim 1 in which the clip includes spaced ears each having a screw hole.

4. The implant of claim 3 in which the clip further includes upper and lower spaced spring arms interconnecting the spaced ears.

5. The implant of claim 4 in which each spring arm includes an outwardly curved portion including a central cut out and the spacer body main section includes spaced upper and lower surfaces each received in a said cut out of the clip.

6. The implant of claim 1 in which the biocompatible, biodegradable material includes polyglycolic acid and/or polylactic acid.

7. The implant of claim 1 in which the spacer body main section includes at least two spaced bony growth orifices.

8. The implant of claim 1 in which the spacer body main section has an isosceles trapezoid cross sectional shape.

9. The implant of claim 1 in which the fins are angled inwardly making the top of the implant longer than the bottom.

10. The implant of claim 1 in which there is a top and a bottom connector for each fin.

11. The implant of claim 10 in which the connectors are cuttable to customize the length of the implant.

12. A tibial tuberosity advancement implant comprising:
    a spacer body made of biocompatible biodegradable material and including:
        a main section having a trapezoid cross sectional shape with at least one bony growth orifice therethrough, and
        inwardly angled fins extending from the main section rendering the top of the implant longer than the bottom; and a clip engageable with the main section and including spaced screw holes for securing the spacer body to the advanced tibial tuberosity and the tibia.

* * * * *